United States Patent [19]
Riedel et al.

[11] Patent Number: 4,812,037
[45] Date of Patent: Mar. 14, 1989

[54] METHOD AND APPARATUS FOR OPTICALLY DETECTING CIRCUIT MALFUNCTIONS

[75] Inventors: Ernest P. Riedel, Murrysville, Pa.; Robert A. Boenning, Timonium, Md.

[73] Assignee: Westinghouse Electric Corp., Pittsburgh, Pa.

[21] Appl. No.: 166,946

[22] Filed: Mar. 11, 1988

[51] Int. Cl.$^4$ ............................................. G01N 21/23
[52] U.S. Cl. ........................................ 356/35; 324/96; 324/501; 356/365
[58] Field of Search .................... 356/35, 364, 365; 324/96, 501

[56] References Cited

U.S. PATENT DOCUMENTS 3,934,199 1/1976 Channin .......................... 324/96 X
4,428,017 1/1984 Vaerewyck et al. ............. 324/96 X Primary Examiner—Davis L. Willis
Assistant Examiner—Matthew W. Koren
Attorney, Agent, or Firm—J. C. Spadacene

[57] ABSTRACT

An apparatus for optically detecting electronic circuit malfunctions includes a light transmitting plate member which is adapted to be positioned adjacent to a plurality of individual electronic circuit elements positioned on a printed circuit board. First and second polarizing filters are positioned adjacent to opposing edges of the light transmitting plate. As the individual electronic circuit elements positioned on the circuit board are operated, the nonuniform heating of the light transmitting plate by the circuit elements produces mechanical stresses within the plate. As monochromatic or white light is passed through the pair of polarizing filters and the light transmitting plate, a light/dark striated pattern of light is produced on the surface of the second polarizing filter. By recording the pattern of a properly operating printed circuit board, a reference pattern may be obtained. Subsequent patterns of light are compared to the reference pattern in order to detect differences between patterns. These differences indicate a change in the temperature of an electronic circuit element with respect to its proper operating temperature, and further indicates a possible malfunction of that individual circuit element.

10 Claims, 1 Drawing Sheet

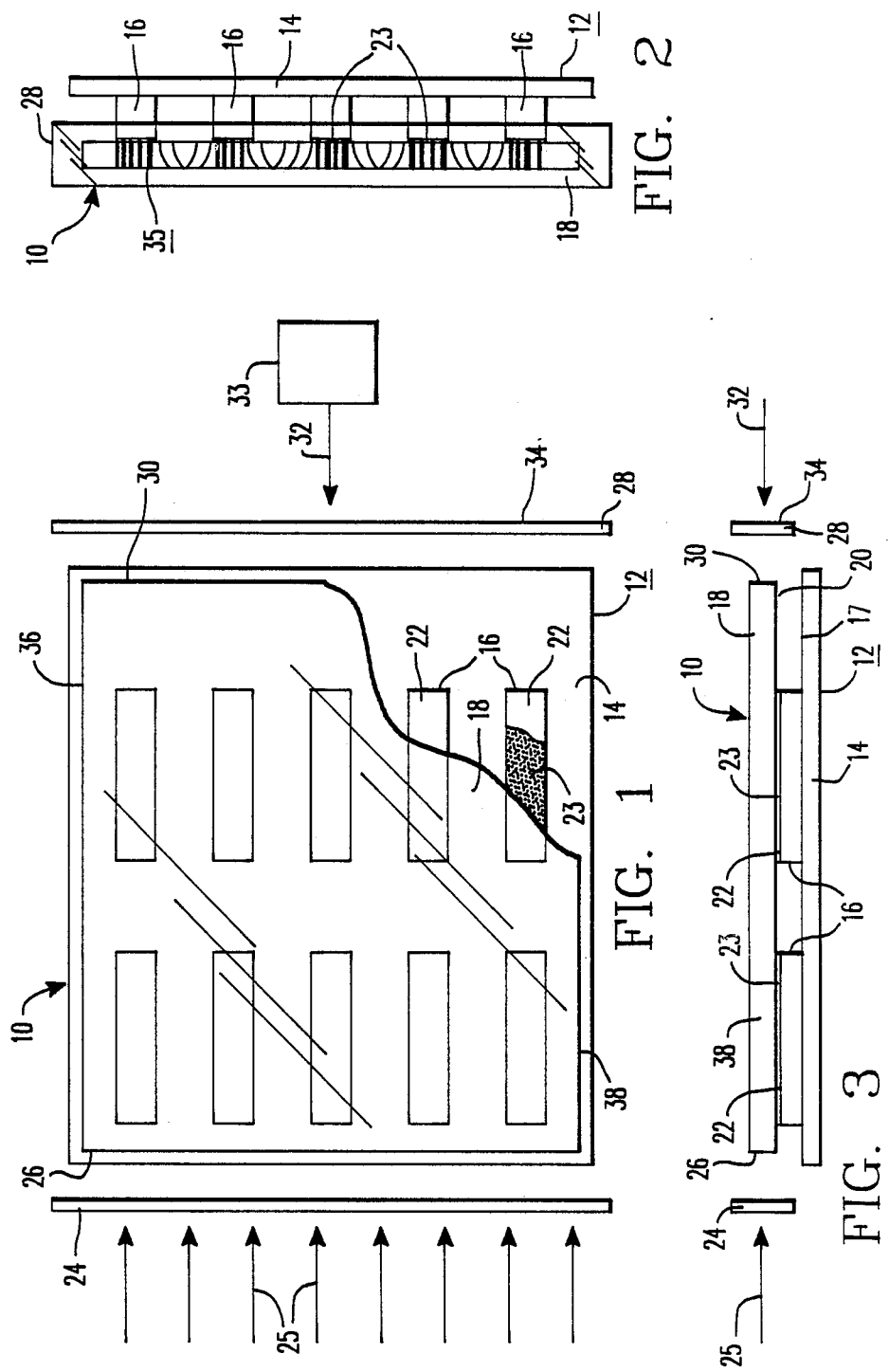

METHOD AND APPARATUS FOR OPTICALLY DETECTING CIRCUIT MALFUNCTIONS

BACKGROUND OF THE INVENTION

This invention relates generally to apparatus for detecting circuit malfunctions, and more particularly, to apparatus for detecting malfunctions in electronic components during operation utilizing optical techniques. The apparatus may also be used to test electronic components prior to their use as a part of a complex electronics system.

Since most conventional electronics systems presently utilized include a plurality of individual printed circuit boards each supporting a large number of individual integrated circuit components, rapidly detecting and pinpointing the exact location of an integrated circuit component malfunction on a single printed circuit board is indeed a difficult task. Normally, most integrated circuit component malfunctions which may develop remain undetected until the affected component eventually fails in service. This requires an unscheduled shutdown of at least the affected portion of the system so that the failed component may be located and either repaired or replaced.

In view of the problems which presently result from individual component failures in complex electronics systems, there is a need for an apparatus capable of detecting and locating component malfunctions prior to failure.

SUMMARY OF THE INVENTION

In accordance with the present invention, there is provided an apparatus for optically detecting electronic circuit malfunctions which includes a sheet of optical material which exhibits stress induced birefringence. Means is provided for positioning the optical material adjacent to an electronic circuit. Means is also provided for directing a polarized light beam onto a first edge of the optical material such that the light beam passes through the optical material. A polarizing filter positioned adjacent to an opposing edge of the optical material receives the light beam emitted from the opposing edge of the optical material and produces a striated pattern of light representative of the temperature distribution in the optical material. Means is provided for recording and comparing the striated pattern of light with a predetermined reference pattern of light. An observed difference between patterns indicates an undesired temperature distribution in the optical material and is representative of an electronic circuit malfunction. For simplicity, it will be assumed herein that the striated pattern of light and the reference pattern are both recorded under steady-state conditions; i.e., the change in temperature with respect to time at any point is zero.

Further in accordance with the present invention, there is provided a method for optically detecting an electronic circuit malfunction which includes the steps of placing a sheet of optical material which exhibits stress induced birefringence adjacent to an electronic circuit. Thereafter, a polarized light beam is directed onto a first edge of the optical material such that the light beam passes through the optical material. The light beam emitted from an opposing edge of the optical material is passed through a polarizing filter thereby producing a striated pattern of light representative of the temperature distribution in the optical material. A reference pattern of light is provided, and the reference and striated patterns of light are compared to detect a difference between patterns. An observed difference indicates an undesired temperature distribution in the optical material and is representative of an electronic circuit malfunction.

Still further in accordance with the present invention, there is provided a method for optically detecting an electronic circuit malfunction which includes the steps of placing a sheet of optical material which exhibits stress-induced birefringence adjacent to a properly operating first electronic circuit. Thereafter, a polarized light beam is directed onto a first edge of the optical material such that the light beam passes through the material. The light beam emitted from an opposing edge of the optical material is passed through a polarizing filter, thereby producing a first, reference striated pattern of light representative of the temperature distribution in the optical material. A sheet of optical material is placed adjacent to a second electronic circuit, and a polarized light beam is directed onto the first edge of the optical material such that the light beam passes through the material. The light beam emitted from the opposing edge of the optical material is passed through a polarizing filter, thereby producing a second striated pattern of light representative of the temperature distribution in the optical material. The first and second striated patterns of light are compared to detect a difference between the patterns. An observed difference between the first and second striated patterns indicates an undesired temperature distribution in the optical material in contact with the second electronic circuit and is representative of a malfunction within the second electronic circuit.

BRIEF DESCRIPTION OF THE DRAWINGS

FIG. 1 is a partial fragmentary top plan view of a detection apparatus of the present invention, illustrating a light transmitting plate member which exhibits stress-induced birefringence positioned above a printed circuit board and a pair of polarizing filters positioned at opposite sides of the circuit board.

FIG. 2 is a view in side elevation of the detection apparatus of FIG. 1, illustrating the striated pattern of light produced by the light transmitting plate member as the plate member is thermally stressed.

FIG. 3 is another view in side elevation of the detection circuit of FIG. 1, illustrating the preferred positioning of the light transmitting plate member and polarizing filters with respect to the heat producing circuit elements positioned on the printed circuit board.

DESCRIPTION OF THE PREFERRED EMBODIMENTS

Referring to the drawings, and particularly to FIGS. 1 and 3, there is illustrated an apparatus generally designated by the numeral 10 for detecting malfunctioning electronic circuit elements positioned on a circuit board utilizing optical techniques. Apparatus 10 is adapted for use with an electronic circuit device 12 which includes a printed circuit board 14 having a plurality of individual electronic circuit elements 16 positioned thereon. Apparatus 10 utilizes the heat generated by the plurality of individual electronic circuit elements 16 during their operation to produce a striated light pattern representative of the temperature distribution of the circuit elements 16 on board 14. As will be described later in greater detail, changes or differences in the temperature distribution of these elements from a reference temperature distribution indicate an individual electronic circuit element 16 malfunction. Since a temperature change in a component during its operation may precede total component failure or otherwise indicate that the component is under abnormal stress, apparatus 10 senses these changes in the temperature distributions to operate as an incipient failure detector.

During proper operation, an electronic system comprised of, for example, a number of circuit boards 14 each having a plurality of individual electronic circuit elements 16 positioned thereon, operates with a characteristic normal spatial temperature distribution over the elements positioned on each board. Apparatus 10 detects deviations from this normal temperature distribution by observing changes in an optical stress birefringent pattern caused by changes in the temperature distribution as an individual element 16 on a given printed circuit board 14 malfunctions. Once detecting apparatus 10 has located an electronic circuit element 16 malfunction or incipient malfunction, the malfunctioning element may be easily replaced during a scheduled system shutdown.

As seen in FIGS. 1 and 3, detecting apparatus 10 includes a light transmitting plate 18 positioned to provide that its bottom surface 20 either contacts or lies adjacent to the top surfaces 22 of the plurality of electronic circuit elements 16. Plate 18 may be formed from a fused silica glass or Lucite acrylic material, and has the property of becoming doubly refracting when subjected to mechanical stress. Mechanical stress will exist in plate 18 if it is subjected to nonuniform heating by the plurality of elements 16, thereby causing the plate to become doubly refracting or birefringent. Although plate 18 is illustrated in FIGS. 1 and 3 as contacting the top surfaces 22 of the plurality of individual electronic circuit elements 16, it should be understood that if plate 18 is spaced from circuit elements 16, the separation between plate 18 bottom surface 20 and the top surfaces 22 of the circuit elements 16 must be sufficiently small to permit the heat generated by each of the circuit elements 16 to be effectively transferred to plate 18. A layer of commercially available heat-conducting silicon grease 23 should be placed between plate 18 bottom surface 20 and the top surfaces 22 of the circuit elements 16 to maximize the heat transferred to the plate.

As seen in FIGS. 1 and 3, optical detecting apparatus 10 also includes a first polarizing filter 24 positioned adjacent to the first or rear edge surface 26 of plate 18. First polarizing filter 24 is positioned with its axis of polarization lying in a preselected plane. A second polarizing filter or analyzer 28 is positioned at the second or front edge surface 30 of plate 18 to lie in opposed relation with first polarizing filter 24. Second polarizing filter or analyzer 28 is positioned with its axis of polarization rotated 90° with respect to first polarizing filter 24. As described, first polarizing filter 24 may be positioned with its axis of polarization in any preselected plane parallel with plate 18 first surface 26, and the axis of polarization of second polarizing filter 28 is positioned 90° therefrom.

In order to optically detect an electronic circuit element 16 malfunction, monochromatic or white light illustrated schematically by the arrows 25 is passed through first polarizing filter 24 to illuminate the first or rear edge surface 26 of plate 18. The light is passed through the body of plate 18 to exit plate 18 at second or front edge surface 30. Thereafter, the light is passed through second polarizing filter or analyzer 28.

Since the axis of polarization of second filter 24 is rotated 90° relative to the axis of polarization of first filter 24, essentially no light is transmitted through second polarizing filter 28 so long as plate 18 is free of mechanical stresses. Under this stress-free condition, when second or front edge surface 30 of plate 18 is viewed by a viewing means 33 looking in a direction indicated by the arrow 32, it appears dark. The viewing means may include a camera or visual scanning system which is capable of recording an observed light pattern and/or comparing an observed pattern to a previously recorded pattern. As described, the second edge surface 30 of plate 18 will appear dark when viewed through second polarizing filter or analyzer 28 provided the temperature of plate 18 is uniform and there are no residual stresses in the plate.

However, since the bottom surface 20 of plate 18 is positioned in abutting or adjacent relation with the top surfaces 22 of the spaced-apart integrated circuit elements 16, the heat generated by the individual circuit elements 16 during their operation will be transmitted to the body of plate 18 in a nonuniform manner to set up residual stresses within plate 18.

The mechanical stresses set up within plate 18 due to the nonuniform heating by the plurality of electronic circuit elements 16 may be utilized to detect undesired changes in circuit element temperatures which indicate an element malfunction. As previously described, plate 18 is made from a glass or acrylic material, and these materials become doubly refracting or birefringent when subjected to mechanical stresses. Mechanical stresses will exist in plate 18 due to nonuniform plate heating by the abutting or adjacent circuit elements 16. If the doubly refracting material is placed between the pair of polarizing filters 24, 28 as shown in FIGS. 1 and 3, monochromatic light provided from source 25 will be elliptically polarized by filter 28 after passing through plate 18. In addition, some percentage of the light transmitted through plate 18 will also be transmitted by second polarizing filter 28.

As seen in FIG. 2, the light transmitted by second polarizing filter 28 produces a light/dark striated pattern 35 on the viewing surface 34 of second polarizing filter 28. The light/dark striated pattern of light which may be observed by viewing means 33 looking in a direction indicated by arrow 32 is a result of the nonuniform temperature distribution in plate 18. The striated pattern 35 is a "signature" of the operating temperature distribution taken along a line extending between opposing side faces 36, 38 of plate 18. Although a particular light/dark striated pattern of light 35 is illustrated in FIG. 2, it should be understood that this pattern is meant to be illustrative only.

By recording the light/dark striated pattern produced by properly operating electronic circuit elements 16, a reference signature or pattern may be obtained to which subsequent patterns can be compared. The comparison may either be done visually, photographically, or by other known means such as an electronic bar code-type measuring device. A difference between a subsequent pattern and the reference pattern indicates that a change in the temperature distribution in plate 18 has taken place, which is evidence of an element 16 malfunction.

As previously described, a change in the temperature of an individual electronic circuit element 16 positioned on printed circuit board 14 will cause a corresponding change in the temperature experienced by plate 18 adjacent that element. As the temperature changes, so do the mechanical stresses experienced by the plate at the point adjacent the circuit element 16. This results in a change in the light/dark striated pattern on the viewing surface 34 of analyzer 28. Thus, if the temperature of an element 16 increases abnormally, this is usually an indication of a malfunction. Likewise, a decrease in an element 16 temperature may be an indication of a malfunction. In either case, this change in temperature will be sensed by plate 18 and visually observable at surface 34 of analyzer 28.

As described, optical detecting apparatus 10 is operable to quickly and efficiently detect either upward or downward changes in the operating temperature distribution of a plurality of electronic circuit elements 16 over a period of time. It should be pointed out that a reference signature or pattern should be obtained soon after the plurality of electronic circuit elements 16 are placed in service to obtain a true reference pattern which is not affected by time-dependent degradation of the individual electronic circuit elements. Subsequent temperature distribution patterns may be compared to the "signature" or reference temperature distribution pattern as often as desired in order to detect a pattern change which indicates a circuit element 16 malfunction.

Although optical detecting apparatus 10 has been described herein as a device operable to detect electronic circuit element malfunctions, it may also be utilized as a test device in printed circuit board assembly operations. For example, a first electronic circuit device 12 may be assembled and energized from a test source. Apparatus 10 may thereafter be utilized in the manner previously described to obtain a striated pattern of light representative of the temperature distribution of the elements 16 on board 14. If it is determined that first electronic circuit device 12 operates satisfactorily, the striated pattern of light representing first device 12 may be used as the "signature" or reference pattern.

Striated patterns of light may thereafter be produced for each following device 12 utilizing apparatus 10, and the striated pattern representing each assembled device 12 compared to the reference pattern. As previously described, the comparison may be done either visually, photographically, or by electronic techniques, such as a bar code reading device. A difference between the reference pattern and a particular following pattern indicates that the device 12 represented by the particular pattern is faulty.

It should now be apparent that the optical detecting apparatus is first used to produce a light pattern representative of properly operating integrated circuit components on a PC board. This light pattern, which is illustrative of the temperature distribution of the properly operating components, is referred to as a "signature" or reference pattern. The optical detecting apparatus is thereafter employed as many times as desired to produce subsequent patterns, and the subsequent patterns are compared to the reference pattern. Any observed differences between a given subsequent pattern and the reference pattern represent an undesired change in temperature of an individual electronic circuit component, and further indicates a malfunction or incipient malfunction of that component. As the temperature change is detected, planned shutdown of the system may be scheduled in order to repair or replace the component.

As described, the optical detecting apparatus of the present invention is operable to detect incipient failures in circuit components which form a part of a complex electronics system before the failures actually occur. Since a temperature change in a component during its operation may precede total failure of the component or otherwise indicate that the component is under abnormal stress, apparatus 10 senses the temperature change and allows the component to be repaired or replaced prior to total failure.

In addition to detecting incipient failures, the optical detecting apparatus of the present invention is also useful as a testing device for electronics components prior to their use as a part of a complex electronics system. In a mass production operation in which a plurality of PC boards each having the same electronic components mounted thereon is assembled, the optical detecting apparatus is first used to produce a light pattern illustrative of a properly operating PC board. This light pattern is again referred to as a "signature" or reference light pattern. A light pattern is also produced for each subsequently assembled PC board, and the light pattern representing each board is compared to the reference light pattern. Any observed differences between light patterns indicates a possible PC board malfunction.

Although the present invention has been described in terms of what are at present believed to be its preferred embodiments, it will be apparent to those skilled in the art that various changes may be made without departing from the scope of the invention. It is therefore intended that the appended claims cover such changes.

What is claimed is:

1. A method of optically detecting electronic circuit malfunctions comprising the steps of:
   placing a sheet of optical material, which exhibits stress induced birefringence, adjacent to a first electronic circuit;
   directing a polarized light beam onto a first edge of said optical material, such that said light beam passes through said optical material;
   passing said light beam emitted from an opposing edge of said optical material through a polarizing filter thereby producing a reference striated pattern of light representative of the temperature distribution in said optical material;
   placing said sheet of optical material adjacent to a second electronic circuit;
   directing said polarized light beam onto said first edge of said optical material such that said light beam passes through the optical material;
   passing said light beam emitted from said opposing edge of said optical material through said polarizing filter thereby producing a second striated pattern of light representative of the temperature distribution in said optical material; and
   comparing said reference and second striated patterns of light to detect differences in the temperature distributions of said first and second electronic circuits, said differences identifying a malfunction in said second electronic circuit.

2. The method of claim 1, wherein the axis of polarization of said polarizing filter is, rotated 90° with respect to the axis of polarization of said polarized light beam at said first edge of said optical material.

3. The method of claim 1, wherein said step of comparing said patterns is done visually.

4. The method of claim 1, wherein said step of comparing said patterns is done electronically.

5. The method of claim 1 which includes the further step of placing a heat-conducting material between said sheet of optical material and said first and said second circuits.

6. An apparatus for optically detecting electronic circuit malfunctions comprising:
   a sheet of optical material which exhibits stress induced birefringence;
   means for positioning said optical material adjacent to an electronic circuit;
   means for directing a polarized light beam onto a first edge of said optical material, such that said light beam passes through said optical material;
   a polarizing filter positioned adjacent to an opposing edge of said optical material, said polarizing filter receiving said light beam emitted from said opposing edge of said optical material and producing a striated pattern of light, representative of the temperature distribution in said optical material; and
   means for comparing said striated pattern of light with a predetermined reference pattern of light to detect differences in said patterns, said differences identifying a malfunction in said electronic circuit.

7. An apparatus as recited in claim 6, wherein the axis of polarization of said polarizing filter is rotated 90° with respect to the axis of polarization of said polarized lightbeam at said first edge of said optical material.

8. An apparatus as recited in claim 6, wherein said means for directing said polarized light beam comprises:
   a coherent light source; and
   a second polarizing filter which polarizes light from said coherent light source.

9. A method of optically detecting electronic circuit malfunctions comprising the steps of:
   placing a sheet of optical material, which exhibits stress induced birefringence, adjacent to an electronic circuit;
   directing a polarized light beam into a first edge of said optical material, such that said light beam passes through said optical material;
   passing said light beam emitted from an opposing edge of said optical material through a polarizing filter thereby producing a striated pattern of light representative of the temperature distribution in said optical material; and
   comparing said striated pattern of light with a predetermined reference pattern of light to detect differences in said patterns, said differences identifying a malfunction in said electronic circuit.

10. The method of claim 9 which includes the further step of placing a layer of heat-conducting silicon material between said sheet of optical material and said electronic circuit.

* * * * *